United States Patent [19]

Turner

[11] 4,448,198

[45] May 15, 1984

[54] INVASIVE HYPERTHERMIA APPARATUS AND METHOD

[75] Inventor: Paul F. Turner, North Salt Lake, Utah

[73] Assignee: BSD Medical Corporation, Salt Lake City, Utah

[21] Appl. No.: 305,180

[22] Filed: Sep. 24, 1981

Related U.S. Application Data

[63] Continuation of Ser. No. 50,050, Jun. 19, 1979, abandoned.

[51] Int. Cl.³ .............................................. A61N 5/02
[52] U.S. Cl. ................................................. 128/422
[58] Field of Search .................... 128/422, 804, 420 A

[56] References Cited

U.S. PATENT DOCUMENTS

| | | | |
|---|---|---|---|
| 3,774,620 | 11/1973 | Hansjurgens | 128/420 A |
| 4,095,602 | 6/1978 | Leveen | 128/804 |
| 4,148,321 | 4/1979 | Wyss et al. | 128/420 A |
| 4,285,346 | 8/1981 | Armitage | 128/804 |
| 4,346,715 | 8/1982 | Gammell | 128/804 |

FOREIGN PATENT DOCUMENTS

| | | | |
|---|---|---|---|
| 1143937 | 2/1963 | Fed. Rep. of Germany | 128/804 |
| 2815156 | 10/1978 | Fed. Rep. of Germany | 128/804 |

*Primary Examiner*—William E. Kamm
*Attorney, Agent, or Firm*—Hubbard, Thurman, Turner & Tucker

[57] ABSTRACT

Invasive hyperthermia apparatus includes an electromagnetic energy radiation source, and a plurality of applicators. Each applicator is adapted for insertion into body tissue and radiating electromagnetic energy therein. Interconnected between the applicators and the radiation source are a power splitter and a plurality of line stretchers for providing the applicator with electromagnetic energy in a preselected frequency - phase power relationship. The applicators, power splitter and line stretchers are operative for causing constructive interference between emitted electromagnetic radiation when the applicators are inserted into body tissue in a preselected spaced apart relationship.

11 Claims, 9 Drawing Figures

INVASIVE HYPERTHERMIA APPARATUS AND METHOD

This application is a continuation, of application Ser. No. 050,050, filed June 19, 1979 now abandoned.

The present invention relates generally to heating human or animal tissue (hyperthermia) and more particularly to electromagnetic radiation (EMR) apparatus for heating local areas within such living body tissue.

As is generally known, death, or necrosis, of living tissue cells occurs at temperatures elevated above a normal call temperature. Further, the death rate of such heated tissue is a function of both the temperature to which it is heated and the duration for which the tissue is held at such temperatures.

It is also well known that the elevation of temperature of living tissue can be produced with electromagnetic energy at frequencies greater than about 10 KHz.

It has been reported that some types of malignant cells may be necrostised by heating them to a temperature which is slightly below the temperature injureous to most normal cells. In addition, some types of malignant cells may be selectively heated and necrotised by hyperthermia techniques because masses of these malignant cells typically have considerably poorer blood flow and thus poorer heat dissipation properties than does the surrounding normal tissue. As a result, when normal tissue containing such malignant masses is heated by EMR, the resultant temperature of the malignant mass may be substantially above that of surrounding healthy cells.

Although some disagreement exists regarding exact temperatures, most malignant cells have a relatively limited temperature range in which hyperthermia is effective in causing necrosis. Below a threshhold temperature of about 41.5° C. (106.7° F.) insubstantial thermal damage occurs even in those types of malignancies which have a greater sensitivity to temperature than do normal cells. In fact, at temperatures just below this threshhold, growth of some types of malignancies may be stimulated. At temperatures within or above 43° to 45° C. (109.4° to 113° F.) thermal damage to most normal cells occur.

Typically, EMR heating of body tissue is accomplished by holding an EMR radiator, or applicator, adjacent to, or against, exterior portions of a body, the EMR then penetrating and heating subsurface portions of tissue. However, significant amounts of energy are absorbed by surface or epidermis layers which may have to be cooled in order to prevent damage thereto by overheating.

The amount of penetration, or the depth of which EMR causes effective heating, is dependent upon the frequency of radiation.

For example, in accordance with an article by A. W. Guy, et al, published in proceedings of the IEEE, volume 63, No. 1, January, 1974 entitled "Therapeutic Application of Electromagnetic Power", the depth of penetration in the human muscle and fat at 100 MHz is 6.66 cm (2.62 inches) and 60.4 cm (23.8 inches), respectively, while at 915 MHz the depth of penetration is only 3.04 cm (1.2 inches) and 17.7 cm (6.97 inches), respectively.

In general, the lower the EMR frequency, the larger the applicator must be in order to effectively radiate electromagnetic energy into the tissue and, as a result, applicators for radiating electromagnetic energy below one gigahertz tend to be large in size and cumbersome to handle. Additionally, such applicators are not configured to selectively heat tumors of various sizes and shapes located well beneath the surface layers of the body being irradiated. Further, tumors, or other selected areas, shielded by a layer of boney tissue such as a skull, are different to effectively heat with externally applied EMR.

Invasive EMR applicators, that is, radiators which can be inserted into body tissue to levels adjacent malignant tumors, or other localized growths, for selective heating thereof, may cause nonuniform heating, or "hot spotting" at or near the surface of such applicators because of nonuniform field distributions. Such unwanted "hot spotting" is more likely to cause serious overheating when such invasive applications are operated at higher power levels in order to heat large localized growths using a single applicator. Such growths may be many times the size of the radiating area of an invasive type applicator.

Other problems associated with invasive type EMR radiators relate to the need for sterility or disposability, because such applicators may be contaminated upon use.

The present invention provides electromagnetic hyperthermia apparatus including a plurality of invasive type applicators and a method of using the apparatus to effectively heat relatively large localized areas disposed within living body tissue, without significant hot spotting at or about the applicators. Such localized areas may be located well beneath surface layers of the body tissue.

Electromagnetic hyperthermia apparatus for heating local regions within living body tissue, in accordance with the invention, comprises a radiation source or means for providing electromagnetic radiation to a plurality of applicators. Each of the applicators is adapted for insertion into body tissue and for radiating electromagnetic energy therein.

Means, interconnected between the radiation means and each of the applicators provides the applicators with electromagnetic energy in a preselected frequency-phase-power relationship.

The applicators and the interconnecting means are configured and operative for causing constructive interference between emitted electromagnetic radiation, when the applicators are inserted into the body tissue in a preselected spaced apart relationship.

When the apparatus of the present invention is operated as described below, the power density in the constructive interference region is greater than the sum of the power densities due to each applicator. This increased power density causes greatly enhanced heating of tissue in the constructive interference region. One embodiment of the invention utilizes a plurality "n" of parallel, spaced applicators which are energized with the same frequency, phase and power, to give a maximum power density $n^2$ times greater than that due to a single applicator.

In one embodiment of the invention the interconnecting means includes a line stretcher for varying the phase of the electromagnetic energy provided to each applicator. Additionally, separate means including at least one catheter and a hypodermic needle are provided for inserting and positioning each applicator into body tissue in said spaced apart relationship. The hypodermic needle and catheter are removable from emitting portions of the applicators for enabling the applicators to emit electromagnetic energy without interference thereby.

A method for irradiating local areas within living body tissue utlizes the apparatus of the present invention and includes the steps of inserting a plurality of electromagnetic energy radiating applicators into a body tissue with each said applicator being inserted in a preselected spaced apart relationship, and, providing the applicators with electromagnetic energy in a preselected frequency-phase power relationship.

A preferred method includes the step of inserting a plurality of "n" similar applicators into body tissue in a preselected pattern around a tissue region to be irradiation heated and providing electro-magnetic energy simultaneously to each of the "n" applicators in a preselected frequnecy-phase-power relationship, thereby causing a subregion of constructive interference heating within the surrounded tissue in which the heating power density is greater than the sum of the power densities due to each applicator.

Other advantages and features of the invention will appear from the following description when considered in connection with the accompanying drawings, in which:

FIG. 1 is a representation, partly in perspective and partially in block diagram form, of an exemplary embodiment of hyperthermia apparatus for heating local areas within living body tissue, and generally showing an electromagnetic radiation (EMR) source, a power splitter, a plurality of line stretchers and a plurality of invasive type applicators, the applicators being shown inserted in a preselected spaced apart relationship to enable constructive interference between emitted electromagnetic radiation therefrom; also shown, although not part of the present invention, are a plurality of temperature probes interconnected with a temperature control for maintaining a preselected temperature within and about the localized area by controlling the power provided by the EMR source.

FIG. 4 shows an applicator inserted into a small tumor or mass and a representation of the heating pattern and field about the applicator to;

Figure 1:
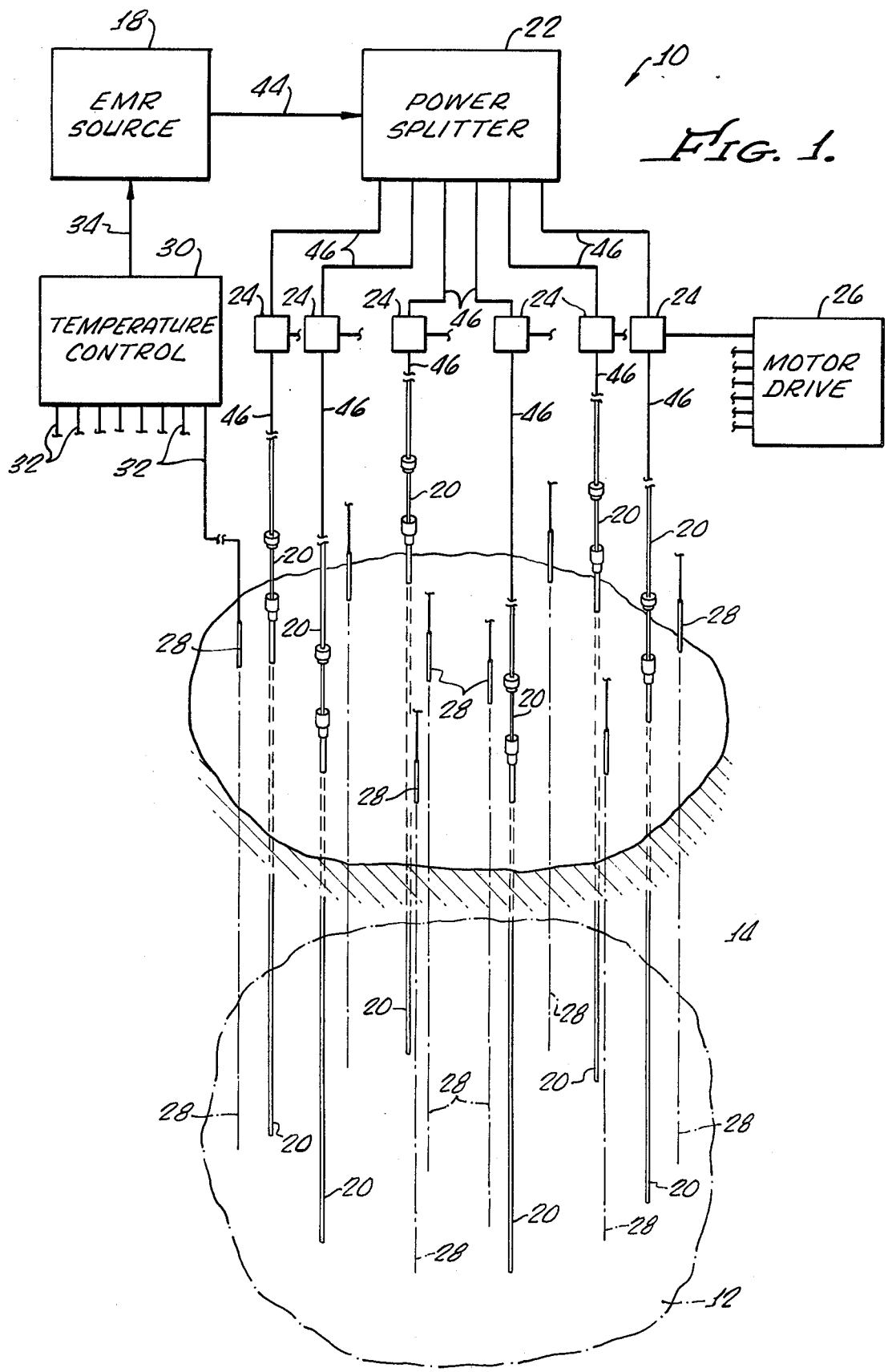
Figure 6:
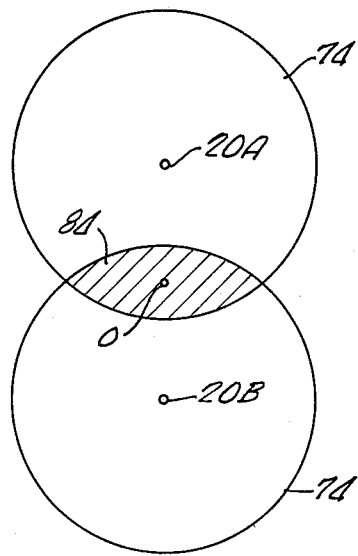
FIG. 6 is a plan view of two substantially parallel applicators positioned so that constructive interference will occur therebetween.
Figure 7:
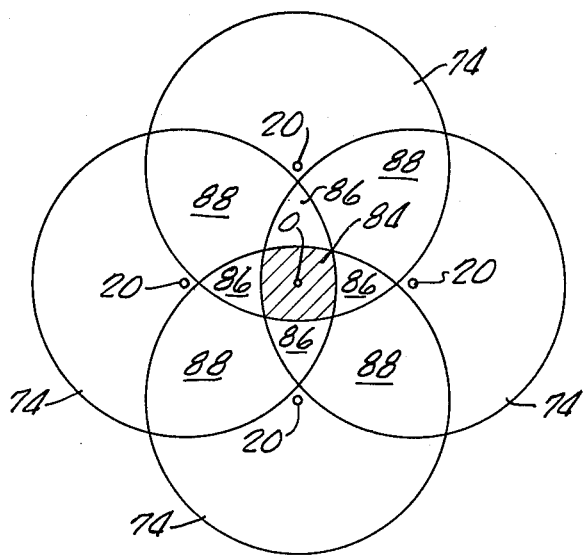
FIG. 7 is similar to FIG. 6 with an array of four substantially parallel applicators being represented along with the field and heating patterns therebetween showing constructive interference.
Figure 8:
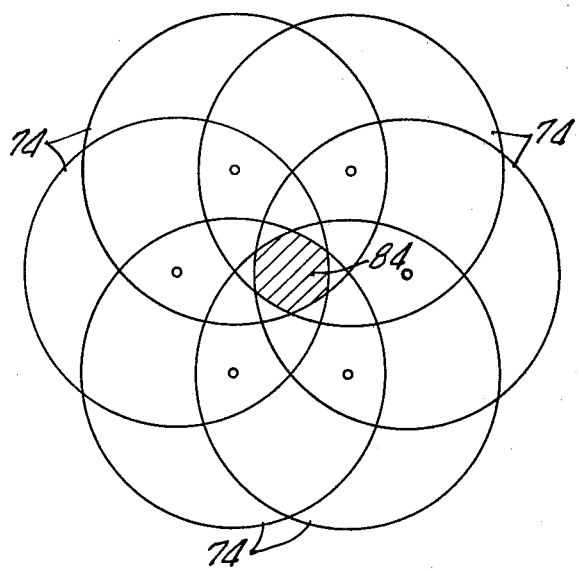
Figure 9A:
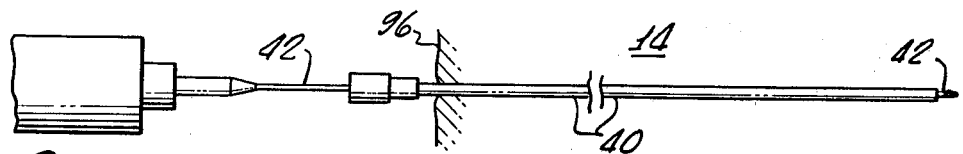
Figure 9B:
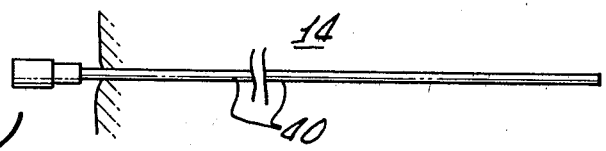
Figure 9C:
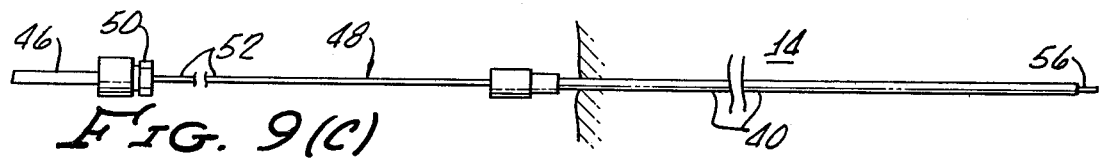
Figure 9D:
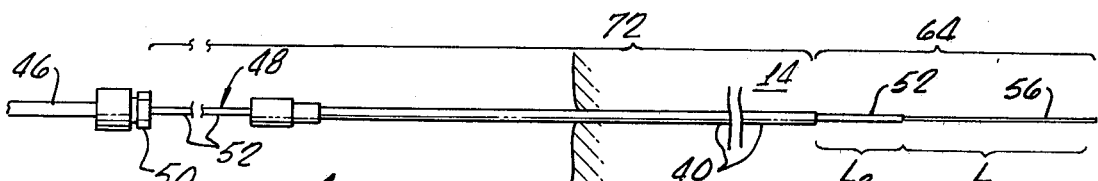

FIG. 8 is similar to FIGS. 6 and 7 except that an array of six substantially parallel applicators is shown; and, FIG. 9 shows in stepwise fashion, the use of the separate means for inserting and positioning each applicator in a predetermined spaced apart relationship in order to cause constructive interference therebetween when each applicator is provided with electromagnetic energy in a preselected frequency-phase relationship, FIG. 9(a) showing insertion of a catheter with a hypodermic needle, FIG. 9(b) showing removal of the hypodermic needle leaving the catheter in place, FIG. 9(c) showing insertion of an applicator into the catheter and FIG. 9(d) showing the catheter partially withdrawn to expose a radiating portion of the applicator Referring now to FIG. 1, electromagnetic hyperthermia apparatus 10 for heating local area, or growth 12, within living body tissue 14, generally includes an electrogmagnetic radiation (EMR) source, or radiation means, 18 for providing electromagnetic energy to a plurality of applicators 20. As hereinafter discussed in greater detail, each of the applicators 20 is adapted for insertion into the body tissue 14 and for radiating electromagnetic energy therein. It is to be appreciated that although six applicators are shown in FIG. 1 the invention is not limited thereto.

Interconnected between the EMR source 18 and each of the applicators 20 is a power splitter 22 and a line stretcher 24 for providing the applicators 20 with electromagnetic energy in a preselected frequency—phase relationship. Further, as will be hereinafter discussed in greater detail, the applicators 20, the power splitter 22 and the line stretchers 24, are configured and operative for causing constructive interference between emitted electromagnetic radiation when the applicators are inserted into the body tissue 14 in a preselected spaced apart relationship. A motor drive 26 interconnected with each line stretcher 24 provides a means for continuously varying the relative phase of electromagnetic radiation provided to each applicator 20.

Also shown in FIG. 1, although not part of the present invention, are a plurality of temperature probes, or sensors, 28, each communicating with a temperature controller 30 via lines 32. The temperature controller 30 is operative, in response to the temperature probes, 28 for controlling the EMR source 18 via an interconnecting cable 34, in order to maintain the probes 28 at preselected temperatures. A plurality of temperature probes is preferred in order to monitor and control not only temperatures within the growth 12, but of normal tissue 14 just outside the growth.

It is to be appreciated that such sensors 28 should be of a type which do not interfere, or absorb, electromagnetic energy, otherwise correct tissue temperatures will not be ascertained. Such sensors may be of a thermister type utilizing carbon-impregnated plastic leads, optical type with connecting optical fibers, or a liquid crystal type as generally described by Cetas, T. C. in PROCEEDINGS OF THE INTERNATION CONFERENCE ON CANCER THERAPY, HYPERTHERMIA AND RADIATION, Apr. 28–30, 1975, Washington, D.C. (Am. Coll. of Radiology, Chevy Chase, Md.).

Figure 2:
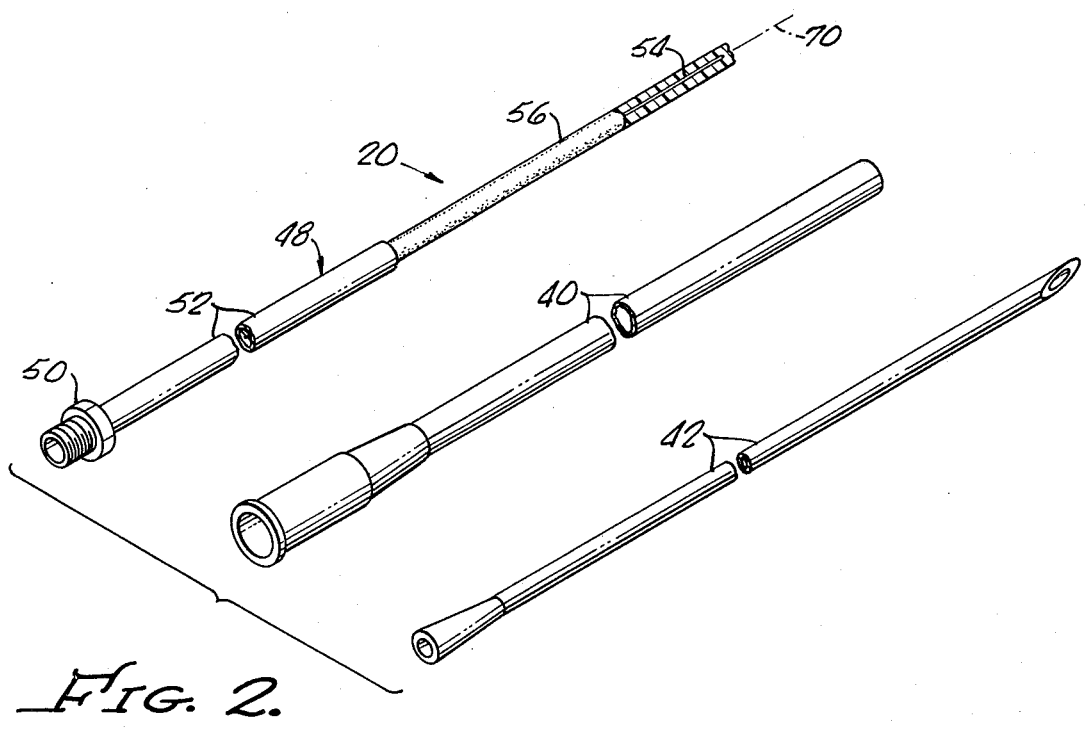
FIG. 2 is an enlarged perspective view of an individual invasive type applicator along with a hypodermic type needle and a catheter used for inserting and positioning each applicator into body tissue in a predetermined spaced apart relationship.

Included in the present invention, and shown in FIG. 2, are a catheter 40 and a hypodermic-type needle 42 which are separate from each of the applicators 20 and provide means for inserting and positioning each applicator into the body tissue 14 in or about the growth 12 in a preselected spaced spart relationship, thereby enabling constructive interference between electromagnetic radiation emitted from each applicator.

Turning again to FIG. 1, the EMR source 18 may be of a single frequency type, however, to provide flexibility in accommodation of applicators 20 having varying operational frequencies, a variable frequency source is preferred such as a model 15152 RF power generator manufactured by MCL, Inc. (Microwave Components Laboratory), which has a frequency range of 10 MHz to 2500 MHz and a power output of approximately 100 watts.

Tje EMR source 18 is connected to the power splitter 22 via a coaxial cable 44. As shown, the power splitter 22, which may be of reactive type, such as Model D6-1FM manufactured by Microlab/FXR Corporation, splits the electromagnetic energy provided by the EMR source 18 into six separate channels which are fed by separate coaxial lines 46 to each of the applicators 20. The line stretchers 24 are of conventional design, such as Model ST-15N manufactured by Microlab/FXR Corporation, and operate to change the effective length of coaxial connection between the EMR source 18 and each applicator 20, thus changing the relative phase of the electromagnetic energy applied to each applicator. Each line stretcher 24 may be manually tuned or adjusted to change the electromagnetic energy phase, or as shown in FIG. 1, operated by the motor driver 26.

It is anticipated that the average characteristic impedance for the animal body tissue wil be approximately equal to 50 ohms over the frequency range between approximately 50 MHz and 1 GHz. To provide efficient impedance coupling throughout the system, the characteristic impedance of the EMR source 18, the power splitter 22, line stretchers 24 and the coaxial cables 44, 46 have been selected from commercially available equipment having characteristic impedances of 50 ohms.

The applicators 20 are constructed from 50 ohm semi-rigid coaxial cable, as will be hereinafter described in greater particularity, to enhance their coupling with body tissue. Should any mismatch occur, an impedance matching device, or tuner, not shown, may be provided to enhance the efficiency of the apparatus 10.

Referring now to FIG. 2, the applicator 20 includes a modified semi-rigid coaxial cable portion 48 connected to a coaxial connector 50 which may be of an OMS type manufactured by Omni-Spectra, Microwave Connector Division, of Walton, Mass. A variety of connectors, not shown, may be employed to adapt the applicator to the commercially available coaxial cable 46 which connects the applicator to the line stretcher 24.

The semi-rigid coaxial cable, also available from Omni-Spectra, Microwave Connector Division, includes a solid copper outer sheath 52, a center conductor 54 (See also FIG. 3) and an insulating material 56, such as Teflon, therebetween.

A feature of the applicator 20 is that it is constructed of readily available off-the-shelf materials, making it economically feasible to mass produce the applicators, so that they may be disposed after each use.

The applicator 20 structure additionally enables a simple method of inserting the applicator into living tissue not otherwise feasible with larger applicators. For example, the applicator 20 may have an outside diameter as small as 0.034 inches thereby enabling the applicator to be inserted in a standard 18 gauge, medical type catheter 40.

The method of inserting applicators 20 into living tissue, as will be hereinafter discussed in greater detail, and the use of separate means for inserting and positioning each applicator, such as the catheter 40 and hypodermic needle 42, enables the applicator 20 to be thinner than may be necessary if the applicator is fashioned for insertion into body tissue without such separate means.

It is important that the applicator 20 diameter, or gauge, be small in order that excessive normal tissue damage does not occur upon insertion and removal thereof. This is particularly important when a plurality of applicators are inserted in a relatively close spaced array as will be discussed hereinafter with greater particularity.

Figure 3:
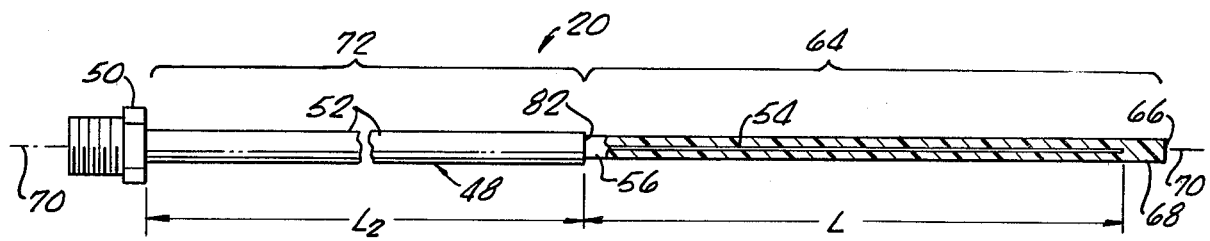
FIG. 3 is an elevation view partially cutaway of an individual applicator showing radiating portions thereof, the invasive type applicator being of a monople type to enhance constructive interference between applicators when they are in a predetermined spaced apart relationship.

As more clearly shown in FIG. 3, a radiating portion 64 is formed on each applicator 20 by removing portions of an outer conductor, not shown, leaving the sheath 52 and exposing the insulator 56 containing the center conductor 54. The center conductor terminates short of an end 66 of the insulator 56, a tip portion 68 thereof being sealed to prevent entry of body fluids or tissue when the applicator is inserted into the body tissue 14.

By sealing the tip portion 68, or otherwise forming a closed tip portion, sterilization of the applicator is facilitated, hence making the applicator 20 reusable, thus possibly lowering the total operational cost of the apparatus 10 when it is employed to irradiate growths or tumors 12 in a number of different animal bodies. The insulator surrounding the center conductor 54 prevents direct contact of the center conductor with body tissue when the applicator is inserted therein, thereby decreasing leakage current, at low frequency, or D.C. offset from the EMR source 18, if present.

The length of the radiating portion 64 is determined in part by the desired operating frequency of the applicator 20 and the dielectric characteristic of the tissue being radiated. The applicator, being of a monopole type, more efficiently radiates electromagnetic energy when the radiating portion 64 has a length approximately equal to a half wave length of the electromagnetic radiation, the wavelength being the wavelength of the electromagnetic energy in body tissue being irradiated. For example, the wavelength of electromagnetic energy of 915 MHz in animal body tissue is approximately 4.46 cm, hence, the length of the radiating portion 64 may be approximately 2.2 cm.

However, the center conductor 54 is not in direct contact with the body tissue 12, the Teflon insulator 56 being disposed therebetween. Since the dielectric constant of the Teflon insulation is approximately 2.0, the effective dielectric constant into which this center conductor radiates is lower than that of the body tissue.

Hence, the length of the radiating portion 64 may be determined empirically by varying the center conductor length, L, until the applicator efficiently radiates energy at a selected frequency, the efficiency being measured in a manner well known in the art by a monitoring reflected power from the applicator 20 while the applicator is inserted into body tissue or a simulation thereof.

Alternatively, the radiating length may be predetermined, and the most efficient operating frequency determined by varying the frequency of the EMR source 18, and selecting the frequency which results in the minimum reflected power. A nonradiating portion 72 of the applicator 20 may have a length, $L_2$, suitable for positioning the radiating portion 64 into or adjacent the growth 12, and for accommodating the catheter 40 as will be hereinafter discussed in connection with the method of inserting the applicators. A convenient length, $L_2$, has been found to be approximately seven inches, although it is not limited thereto.

Figure 4:
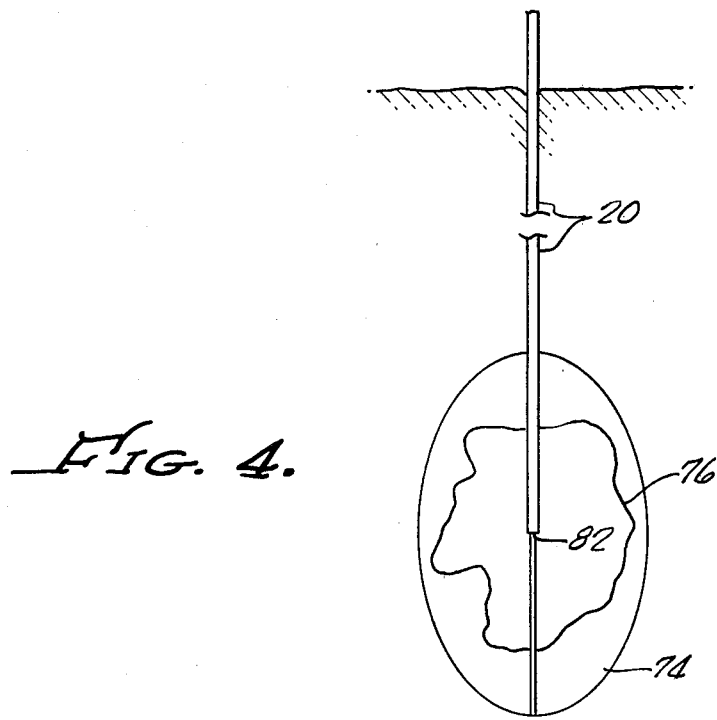

The invasive applicator 20, is of a monopole type with the polarization of the field established thereby being along a longitudinal axis 70 thereof. Electromagnetic energy is emitted in a 360° field pattern about the radiating portion 64 (FIG. 6) and, as such, the intensity of the field diminishes rapidly with the radial distance from the radiating portion 64. FIG. 4 shows a representation of both the approximate field and heating pattern 74 of the applicator 20, the pattern being approximately ellipsoidal in shape.

A small mass, or tumor, 76 may be heated using the applicator 20 with the applicator inserted into the mass with a junction 82 between the radiating portion 64 and the non-radiation portion being positioned approximately at the center of the mass 76. For the small tumor 76, the radiation induced heating area or pattern 74 may engulf the mass with the greatest amount of heating occuring at the junction 82.

However, the applicator 20, when operating at, for example, 915 MHz, may not significantly heat a volume of tissue more than approximately two or three cm in diameter when operating at a power level of approximately 10 watts. As the power to the applicator is increased, to increase the amount of heating and the tissue volume heated, the applicator may cause hot spotting or overheating at or near the junction 82 and along the copper shaft 52. Thus, the applicator is limited in the size of tumor it can effectively heat because of both hot spotting and the range, or penetration, of the electromagnetic energy radiated from the applicator, the latter being a function of the electromagnetic energy frequency.

Significant advantage occurs when a plurality of applicators 20 are used in preselected spaced apart relationship with each applicator being provided with electromagnetic energy in a preselected frequency—phase relationship so as to enable reinforcing field patterns therebetween.

Figure 5:
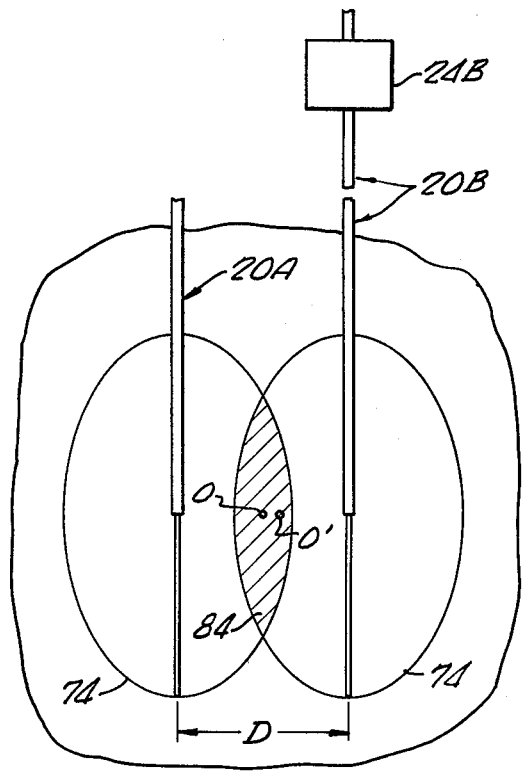
FIG. 5 is a simplified elevation view of two substantially parallel applicators and a representation of the general electromagnetic field generated thereabout with an interference pattern therebetween.

For example, as represented in FIGS. 5 and 6 for two applicators 20A, 20B, when the applicators are spaced apart from one another by one half wavelength, or less, and provided with electromagnetic energy of equal phase, frequency and amplitude, the field 74 from each applicator will be reinforced in an area or volume 84 therebetween, where the fields overlap.

The reinforcement area, or volume, 84 will be located approximately equidistance from each applicator 20A, 20B when the applicators are driven with the electromagnetic energy of the same phase. However, if the phase of the electromagnetic energy provided to the applicator 20B, for example, is caused to lag that of the electromagnetic energy provided to applicator 20A, by a line stretcher 24b, the reinforcement patterns will shift toward the lagging applicator 20B. The amount of shift is proportional to $PS/(2° \times 360°)$ $(\lambda)$, where PS is the amount of phase shift in degrees, and $\lambda$ is the wavelength of the electromagnetic radiation in the tissue 12.

Hence, for a shift of 45°, a center point, 0, representing the position of the reinforcement area 84, will shift approximately 0.3 cm when the applicators are driven at 915 MHz, which corresponds to a wavelength in animal body tissue of approximately 4.5 cm. As hereinafter discussed in greater detail, the shifting of the reinforcement area by phase adjustment is important in preventing hot spotting when a greater number of applicators 20 are used in an array.

It should be appreciated that because the radiated electromagnetic energy is absorbed by the tissue, the only volume where field reinforcement occurs is between the applicators. That is, significant field from one applicator 20A does not extend beyond the second applicator 20B when the two applicators are spaced apart by a distance "D" of one half wavelength, or 2.23 cm when radiating 915 MHz electromagnetic energy. This results from the fact that at a one-half wavelength distance from an applicator 20, the field power density is reduced to approximately ¼ the power density at a ¼ wavelength distance due to divergence and absorption. In some instances, depending, in part, on the type of tissue, the applicators may be spaced up to a distance equal to three quarters of a wavelength.

In general for N number of applicators 20 driven with equal phase and amplitude, the power density, $P_n$ at the point, 0, spaced equidistant from each applicator 20, see also FIGS. 7 and 8, is directly proportional to the square of the total voltage density $V_n$ at the point 0.

$$P_n \sim (V_n)^2. \tag{1}$$

When the applicators 20 are spaced symmetrically about the point, 0, the polarization and phase of the voltage density vector V with peak voltage V from each applicator, is equal at point 0.

The total voltage density $V_n$ at the point 0 is the sum of all the arriving sources. Since they are of equal phase and amplitude, the total voltage density at point 0 is, $$V_n = NV \tag{2}$$

Hence the power density at point 0 for one applicator 20 is, $$P_l \sim V^2 \tag{3}$$

whereas the power density at point 0 for N applicators 20 is $$P_n \sim N^2 V^2 \tag{4}$$

A power improvement factor, F, may be defined as the ratio of the power density at point 0 for N application 20 to the power density at point 0 for one applicator, or $$F = (P_n/P_l) = (N^2 V^2/V^2) = N^2 \tag{5}$$

It is then easily seen that the use of six applicators, for example, (FIG. 8) results in a power improvement factor, at point 0, of 36. In effect, the use of a plurality of applicators in an array as described, produces a synergistic result when the applicators are driven with electromagnetic energy of equal frequency, phase and amplitude.

FIGS. 6, 7 and 8 illustrate the reinforcement field, and constructive interference patterns using, respectively 2, 4 and 6 applicators 20 in a spaced array wherein each applicator is approximately equally spaced on the circumference of a circle having a center point, 0, and a diameter approximately one half wave length of electromagnetic energy in animal tissue.

The wavelength of electromagnetic energy in body tissue of high water content, such as muscle or tumors, is approximately as follows:

| Frequency | Typical wavelengths |
|---|---|
| 300 MHz | 11.9 cm |
| 433 | 8.76 |

| Frequency | Typical wavelengths |
|---|---|
| 750 | 5.34 |
| 915 | 4.46 |
| 1500 | 2.81 |
| 2450 | 1.76 |

It is apparent from the above frequency/wavelength relationship, that for an approximately 2.5 cm circular array, a frequency of 915 MHz or less should be used.

For clarity of presentation, only the reinforcement area 84 having the greatest improvement factor, F, is shown shaded for each of the applicator 20 arrays shown in FIGS. 6, 7 and 8.

It should be appreciated that, for example, in an array of four applicators shown in FIG. 7, several reinforcement areas 84, 86, 88 occur. The reinforcement areas 84, 86, 88 are created by the combinations of the electromagnetic fields from four, three, and two applicators respectively. In combination, the areas 84, 86, 88 represent the total area between the applicators where enhanced heating is enabled by the use of a plurality of applicators 20 being driven with electromagnetic energy of the same frequency, power and phase while in a preselected spaced apart relationship.

It is important to recognize that through the use of multiple applicators 20 not only can a larger volume of tissue be heated, but that each applicator may be operated at a power level low enough to essentially eliminate the problem of hot spotting, or overheating of tissue at or near the junction 82 and along the shaft 52 of each applicator.

However, because of the reinforcement field areas, a central hot spot may develop at the center, 0, of an array of applicators 20. To prevent such hot spotting and to further spread or cause more uniform heating between applicators 20 in an array, the phase of electromagnetic energy provided to each applicator 20 may be continuously varied by the line stretchers 24 via the motor drive 26, which in turn, continuously shifts the field reinforcement areas. It should be appreciated that the greater the number of applicators in an array, the greater the need for shifting the reinforcement areas if more uniform heating is desired.

Additionally, while the applicators 20 may be driven at the same frequency, phase and power, it may be preferable to alter the frequency, phase or power provided to each applicator in order to vary the extent and shape of the reinforced field pattern as may be desirable for different shaped tumor masses.

The applicator may be inserted into the spaced apart relationship within and/or around the growth 12 by means of the hypodermic needle 42 and the catheter 40 as hereinafter described. A jig, not shown, may be used to hold and adjust the applicators 20 in an appropriate manner to insure that the applicators are positioned properly for irradiating the growth.

Additionally, the position of the applicators may be determined, before electromagnetic energy is applied thereto, by x-ray methods, or the like.

The use of the hypodermic needle 42 and catheter 40 in inserting each applicator 20 is illustrated in FIGS. 9a, 9b, 9c and 9d. FIG. 9a shows the insertion of the hypodermic needle 42 along with the catheter thereabout to a preselected depth below a tissue surface 96. After insertion, the hypodermic needle is removed, leaving the catheter in the tissue. (FIG. 9b).

Next, as shown in FIG. 9c, the applicator 20 is inserted into the catheter 40, the applicator being configured for insertion into a small gauge catheter as hereinbefore described. Before electromagnetic energy is provided to the applicator, the catheter 40; is slid outwardly from the body tissue 14, to a position along the non-radiating portion 72 of the applicator, thus exposing the applicator radiating portion 64 and enabling the applicator to radiate into the body tissue 14, and growth 12, without interference thereby. (FIG. 9b).

To insure that the cathether does not disturb the radiated field pattern, the catheter is preferably withdrawn far enough to expose a length $L_3$ of the applicator non-radiating portion 72 which is equal to, or greater than, approximately one half of the length, L, of the center conductor 54 and applicator radiating portion 64.

Although there has been described above a particular arrangement of an apparatus and a method for irradiating human or animal tissue in accordance with the invention for the purpose of illustrating the manner in which the invention may be used to advantage, it will be appreciated that the invention is not limited thereto. Accordingly, any and all modifications variations or equivalent arrangements which may occur to those skilled in the art, should be considered to be within the scope of the invention as defined in the appended claims.

What is claimed is:

1. Electromagnetic hyperthermia apparatus for heating local regions within body tissue comprising:
    (a) a source of electromagnetic radiation;
    (b) a plurality of electromagnetic energy radiating applicators, wherein said applicators are inserted into the body tissue in a preselected pattern, and further wherein said applicators are substantially parallel; and
    (c) means interconnected between the radiation source and each of said applicators for continuously providing each said applicator with electromagnetic energy having the same frequency and preselected relative phase and power relationships, wherein the radiation emitted by said applicators undergoes constructive interference in the local region to be heated.

2. The hyperthermia apparatus of claim 1, wherein said interconnected means comprises a power splitter, wherein the electromagnetic energy supplied to each of said applicators has the same relative phase and power.

3. The hyperthermia apparatus of claim 1, wherein said interconnected means comprises;
    a power splitter coupled to said applicators and to said source; and
    means coupled to said power splitter for controlling the relative phase of the electromagnetic energy applied to each of said applicators.

4. The hyperthermia apparatus of claim 3, wherein said controlling means comprises a plurality of line stretchers.

5. The hyperthermia apparatus of claim 3, wherein said controlling means comprises means for continuously varying the relative phase of the electromagnetic energy applied to said applicators.

6. The hyperthermia apparatus of claim 1, wherein said applicators are spaced so as to define the circumference of a circle.

7. The hyperthermia apparatus of claim 6, wherein the diameter of the cicle is no more than approximately three-quaters of a wavelength of the electromagnetic radiation in the tissue.

8. Electromagnetic hyperthermia apparatus for heating local regions within body tissue, comprising:
   a source of electromagnetic radiation;
   a plurality of individual electromagnetic energy radiators suitable for substantially parallel insertion into the body tissue so as to define points equally spaced on the circumference of a circle;
   a power splitter coupled to said source; and
   a plurality of line stretchers coupled between said power splitter and said applicators, wherein the relative phase of energy supplied to said applicators is controlled by said line stretchers.

9. A method for heating local regions within body tissue with electromagnetic radiation, comprising the steps of:
   (a) inserting a plurality of electromagnetic energy radiating applicators into the body tissue in a substantially parallel, spaced apart relationship; and
   (b) simultaneously providing all of the applicators with electromagnetic energy having aligned fields, the same frequency, and preselected relative phase and power relationships.

10. The method of claim 9, wherein step (b) comprises the step of simultaneously providing all of the applicators with electromagnetic energy having the same frequenc, relative phase and power.

11. The method of claim 9 further comprising the step of:
   (c) continuously varying the relative phase of the electromagnetic energy provided to the applicators.

* * * * *